(12) United States Patent
Old et al.

(10) Patent No.: US 7,259,235 B2
(45) Date of Patent: Aug. 21, 2007

(54) METHOD FOR GENERATING AN IMMUNE RESPONSE AND REAGENTS THEREFOR

(75) Inventors: Lloyd J. Old, New York, NY (US); Sacha Gnjatic, New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 569 days.

(21) Appl. No.: 10/493,405

(22) PCT Filed: Sep. 26, 2002

(86) PCT No.: PCT/US03/30473

§ 371 (c)(1),
(2), (4) Date: Apr. 22, 2004

(87) PCT Pub. No.: WO2004/029274

PCT Pub. Date: Apr. 8, 2004

(65) Prior Publication Data
US 2006/0204507 A1    Sep. 14, 2006

Related U.S. Application Data

(60) Provisional application No. 60/414,046, filed on Sep. 27, 2002.

(51) Int. Cl.
*C07K 14/435* (2006.01)
*C07K 7/06* (2006.01)
*C07K 7/08* (2006.01)
*C07K 14/74* (2006.01)

(52) U.S. Cl. ............ 530/324; 530/325; 530/326; 530/327; 530/328; 530/350; 530/402; 530/403

(58) Field of Classification Search ............ None
See application file for complete search history.

(56) References Cited

U.S. PATENT DOCUMENTS 6,210,886 B1 * 4/2001 Van Baren et al. ............ 435/6
6,251,603 B1 * 6/2001 Jager et al. ................... 435/6

* cited by examiner

*Primary Examiner*—Christina Chan
*Assistant Examiner*—F. Pierre VanderVegt
(74) *Attorney, Agent, or Firm*—Fulbright & Jaworski L.L.P.

(57) ABSTRACT

Isolated peptides are disclosed which, when processed, generate a coordinated immune response.

5 Claims, No Drawings

SEQUENCE LISTING

```
<160> NUMBER OF SEQ ID NOS: 7

<210> SEQ ID NO 1
<211> LENGTH: 9
<212> TYPE: PRT
<213> ORGANISM: H. sapiens

<400> SEQUENCE: 1

Ser Leu Leu Met Trp Ile Thr Gln Cys
1               5

<210> SEQ ID NO 2
<211> LENGTH: 11
<212> TYPE: PRT
<213> ORGANISM: H. sapiens

<400> SEQUENCE: 2

Ser Leu Leu Met Trp Ile Thr Gln Cys Phe Leu
1               5                   10

<210> SEQ ID NO 3
<211> LENGTH: 9
<212> TYPE: PRT
<213> ORGANISM: H. sapiens

<400> SEQUENCE: 3

Leu Met Trp Ile Thr Gln Cys Phe Leu
1               5

<210> SEQ ID NO 4
<211> LENGTH: 30
<212> TYPE: PRT
<213> ORGANISM: H. sapiens

<400> SEQUENCE: 4

Ala Arg Gly Pro Glu Ser Arg Leu Leu Glu Phe Tyr Leu Ala Met Pro
1               5                   10                  15

Phe Ala Thr Pro Met Glu Ala Glu Leu Ala Arg Arg Ser Leu
            20                  25                  30

<210> SEQ ID NO 5
<211> LENGTH: 30
<212> TYPE: PRT
<213> ORGANISM: H. sapiens

<400> SEQUENCE: 5
```

```
Leu Gln Leu Ser Ile Ser Ser Cys Leu Gln Gln Leu Ser Leu Leu Met
1               5                   10                  15

Trp Ile Thr Gln Cys Phe Leu Pro Val Phe Leu Ala Gln Pro
            20                  25                  30

<210> SEQ ID NO 6
<211> LENGTH: 30
<212> TYPE: PRT
<213> ORGANISM: H. sapiens

<400> SEQUENCE: 6

Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser
            20                  25                  30

<210> SEQ ID NO 7
<211> LENGTH: 32
<212> TYPE: PRT
<213> ORGANISM: H. sapiens

<400> SEQUENCE: 7

His Arg Gln Leu Gln Leu Ser Ile Ser Ser Cys Leu Gln Gln Leu Ser
1               5                   10                  15

Leu Leu Met Trp Ile Thr Gln Cys Phe Leu Pro Val Phe Leu Ala Gln
            20                  25                  30
```

METHOD FOR GENERATING AN IMMUNE RESPONSE AND REAGENTS THEREFOR

RELATED APPLICATION

This application is a continuation-in-part of Ser. No. 60/414,046 filed Sep. 27, 2002, incorporated by reference.

FIELD OF THE INVENTION

This invention relates to methods and products useful in generating immune responses in a subject. In particular, it relates to materials which are based upon the highly immunogenic molecule NY-ESO-1.

"NY-ESO-1" is described in several U.S. Pat. No. 5,804,381, which is incorporated by reference. The '381 patent taught that the molecule is a tumor rejection antigen precursor, a term defined in, e.g., U.S. Pat. No. 5,342,774, also incorporated by reference.

Various peptides have been identified which consist of amino acids contiguous to each other in NY-ESO-1, and which generate immune responses when complexed to appropriate MHC molecules. Exemplary of these are the peptides described in U.S. Pat. No. 6,274,145, and Ser. No. 09/165,546, both of which are incorporated by reference. Variations on these peptides, with good immunological properties, may be found in, e.g. U.S. Pat. No. 6,417,165, also incorporated by reference. Additional materials relevant to NY-ESO-1's immunogenic efficacy may be found at, e.g., Jäger, et al, J. Exp. Med. 187:265 (1988), incorporated by reference. This reference describes, inter alia, three immunogenic NY-ESO-1 peptides. In a follow up paper, i.e., Jäger, et al., Proc. Natl. Acad. Sci USA, 97:4760 (2000), incorporated by reference, these peptides were used to determine the frequency of T cell responses in HLA-A2$^+$ patients with advanced NY-ESO-1$^+$ tumors, and correlated this to antibody presence in patients' sera. Also, see U.S. Pat. No. 6,251,603, incorporated by reference. It was found, essentially, that a substantial proportion of patients had naturally occurring, spontaneous and concomitant antibodies and CD8$^+$ T cell reactivity against NY-ESO-1.

NY-ESO-1 vaccine compositions can be generated using NY-ESO-1 protein or defined immunogenic peptides representing epitopes for CD8$^+$ or CD4$^+$ T cells. See Jager, et al., supra. Protein based vaccine compositions contain the full range of potential peptide epitopes for a particular protein, but represent a substantial manufacturing and production requirement. Peptide based vaccines allow simple manufacture and formulation; however, they risk not producing the full range of potential immunogenic peptide epitopes and might fail in inducing an adequate, wide ranging immune response. A solution to this is to design a vaccine based upon a series of polypeptides derived from a particular antigen such as NY-ESO-1, so that the polypeptides contain the immunogenic portion of that antigen. CD8$^+$ and CD4$^+$ peptide T cell epitopes but such a vaccine provides none of the complexes of manufacturing and production problems associated with proteins.

Further work was carried out, wherein the peptides referred to in Jäger, et al, supra, were injected, together with GM-CSF as an adjuvant, in patients with NY-ESO-1$^+$ carcinoma. See Jager, et al., Proc. Natl. Acad. Sci. USA, 97:12198 (2000), incorporated by reference. The immunization was efficient, and CD8+responses to SEQ ID NOS: 1 and 2, defined supra, could be detected in most of the vaccinated patients who did not show preexisting immunity to NY-ESO-1.

Any work that involves the administration of peptides to patients has to consider one of the "central paradigms" of antigen presentation, which is that, with the exception of select, "professional APCs", such as dendritic cells, proteins which are added endogenously do not enter pathways for epitope loading on MHC Class I molecules. See, e.g., Thery, et al., Curr. Opin. Immunol., 13:45-51 (2001); Heath, et al., Nature Rev. Immunol., 1: 126-134 (2001).

Notwithstanding this "paradigm", it has also been observed that fragments of peptides can act efficiently when added endogenously to non-professional APCs. Polypeptides, generally 15-18 amino acids long, have been used to map regions of a protein recognized by CD8$^+$ T cell lines. See Gnjatic, et al., Proc. Natl. Acad. Sci. USA, 97:10917-10922 (2000); Tobery, et al., J. Immunol Methods, 254:59-66 (2001), incorporated by reference. It was observed that APCs pulsed with these peptides and did, in fact, present short amino acid epitopes, 8-11 amino acids long, with HLA-Class I molecules. See Correale, et al., J. Immunol., 161:3186-3194 (1998). these, in addition to Correale, et al., have shown that longer peptides can be used to obtain MHC Class I restricted T cells. See Renia, et al., Proc. Natl. Acad. Sci. USA, 88:7963-7967 (1991); Yanuck, et al., Cancer Res., 53:3257-3261 (1993). Others, including Niedermann, et al., Immunol Rev., 172:29-48 (1999); and Ayyoule, et al., J. Immunol., 168:1717-1722 (2002), have exposed polypeptides to purified proteasome preparations in order to facilitate Class 1 epitope identification.

The disclosure which follows is concerned with the issues raised by the "paradigm" discussed above, as it applies to NY-ESO-1, as well as issues relating to cross reactivity with the administration of NY-ESO-1 peptides.

These, as well as other features of the invention, will be disclosed in greater detail in the Detailed Description which follows.

DETAILED DESCRIPTION OF PREFERRED EMBODIMENTS

EXAMPLE 1

Peripheral blood lymphocytes were obtained from a subject suffering from Schwannoma, who tested positive for antibodies to NY-ESO-1, using standard techniques. Once the PBLs were obtained, CD8$^+$ T lymphocytes were separated therefrom, by using antibody coated magnetic beads. These were then seeded into round bottomed 96 well plates, at 5×10$^5$ cells/well, in RPMI medium 1640, which had been supplemented with 10% human AB serum, L-glutamine (2 mM), penicillin (100 U/ml), streptomycin (100 µg/ml), and 1% non-essential amino acids.

The PBLs that had been depleted of CD8$^+$ cells were then pulsed with 10 µm of either

```
SLL MWTTQC        (SEQ ID NO: 1)
or

SLLMWITQCFL       (SEQ ID NO: 2)
``` overnight, at 37° C., in 250 ul of serum free medium. The pulsed cells were then washed, irradiated, and then added to CD8$^+$ cells at a concentration of 1×10$^6$ antigen presenting cells (APCs), per well. After 8 hours, IL-2 (10 U/ml), and IL-7 (20 ng/ml) were added to culture wells. The step was repeated every three days until harvest.

The CD8$^+$ cells were then tested in an ELISPOT assay. Flat bottomed, 96 well nitrocellulose plates were coated with IFN-γ specific monoclonal antibodies (2 μg/ml), and incubated overnight at 4° C. After washing with RPMI, the plates were blocked with 10% human AB serum for 2 hours, at 37° C. Presensitized CD8+ cells, prepared as described supra, were added at both 5×10$^4$ and 1×10$^4$ cells/well, together with 5×10$^4$ target cells. The target cells were either cells of melanoma cell line SK-MEL-37 (which expresses NY-ESO-1 mRNA), and had been pulsed with 10 μM of either SEQ ID NO: 1 or 2*. The mixes were incubated for 20 hours in RPMI medium 1640, without serum. The plates were then washed thoroughly with water and 0.05% Tween 20 to remove cells, and 0.2 μg/ml of anti-IFN-γ mAbs, labeled with biotin, were added to the wells. The mixes were incubated for 2 hours, at 37° C., after which the plates were washed and developed with streptavidin-alkaline phosphatase (1 μg/ml), for 1 hour at room temperature. After washing, the substrate 5-bromo-4-chloro-3-indolyl phosphate/nitroblue tetrazolium was added, and incubated for 5 minutes. After final washing steps, plate membranes displayed dark violet spots which were counted under the microscope.

The results indicated that both SEQ ID NO: 1 and SEQ ID NO: 2 were equally recognized, following stimulation with either SEQ ID NO: 1 or SEQ ID NO: 2, showing that the two peptides had either cross reacted or shared some epitope as both immunogen and antigen, showing a response characteristic of previous monitoring studies, as reported by Jäger, et al., *Proc. Natl. Acad. Sci USA,* 97:4760 (2000).

EXAMPLE 2

The experiment reported in example 1, supra, was repeated, with one exception. In the ELISPOT assay, the target cells were changed, using SK-MEL37 cells that had been transfected with a recombinant vaccinia virus which expressed full length NY-ESO-1, as described by Gnjatic, et al., *Proc. Natl. Acad. Sci USA,* 97:10917 (2000), incorporated by reference, using 30 pfu/cell of virus, either wild type vaccinia or recombinant, NY-ESO-1 expressing virus. The results paralleled the results from example 1.

Similar results were obtained when EBV-B cells were used, whether they were pulsed with peptide, or transfected as described.

The results reported supra, differed from results that had been observed in clinical cancer trials using SEQ ID NO: 1 and SEQ ID NO: 2. In these studies, it was observed that patients who did not present NY-ESO-1 specific antibodies prior to immunization often developed reactivity to SEQ ID NO: 2, in the absence of reactivity to SEQ ID NO: 1. If reactivity to SEQ ID NO: 1 did occur at all, it occurred late in the course of vaccination. The discrepancy indicates that SEQ ID NO: 2 can stimulate a specific response that is distinct from SEQ ID NO: 1.

Experiments were carried out to define the response more clearly, and they are described in the examples which follow.

EXAMPLE 3

The peptide:

LMWITQCFL (SEQ ID NO: 3), was synthesized, using standard methods. The peptide was tested in an ELISPOT assay, as described supra, and a patient who responded to SEQ ID NO: 2 but not to SEQ ID NO: 1 was in fact cross reactive. At least in one patient, SEQ ID NO: 2 and 3 had similar antigenic profiles.

To test the extent of the response to SEQ ID NO: 3, peripheral blood lymphocytes were taken from several patients who had been immunized previously with both SEQ ID NOS: 1 and 2 as well as non-immunized subjects who showed antibodies to NY-ESO-1 when tested, and were then expanded, in vitro, by stimulation with peptides of SEQ ID NO: 1, 2 or 3, as described supra, or with cells presenting naturally processed NY-ESO-1 peptides as a result of being transfected with recombinant adenoviruses that encoded full length NY-ESO-1. See Gnjatic, et al., supra, incorporated by reference, for information on the transfection of cells with this construct. Autologous PBLs depleted of CD8+ cells were infected with the adenoviral constructs, at 100 IU/cell, overnight, at 37° C. in 250 μl serum free medium, and processed further, as described supra.

Peptide specific CD8+ cells were then stained with HLA-A2 tetrameric complexes which contained one of SEQ ID NO: 1, 2 or 3. These complexes were synthesized as described by Jäger, et al., *Proc. Natl. Acad. Sci USA,* 97:4760 (2000) and Altman, et al., *Science,* 274:94 (1996), both of which are incorporated by reference. The tetramers were assembled with one of the peptides, and then presensitized CD8+ cells were placed in 50 μl of phosphate buffered saline containing 3% fetal calf serum. These were stained with tetramers that had been labeled with phycoerythrin, for 15 minutes, followed by addition of tricolor CD8+ mAbs, and anti CD62L mAbs, for 15 minutes, on ice. After washing, the results were analyzed by flow cytometry.

Subjects who exhibited a spontaneously induced immune response to NY-ESO-1 and were positive for NY-ESO-1 specific antibodies but had not received any immunization with NY-ESO-1 peptide tested positive only for SEQ ID NO: 1.

A second group of patients, who did not show spontaneous pre-existing NY-ESO-1 immunity, and had no antibodies to NY-ESO-1, and were immunized with both SEQ ID NOS: 1 and 2, possessed CD8+ cells reactive only with SEQ ID NO: 3. In follow up tests, subjects without preexisting immunity who were immunized with SEQ ID NO: 2 did react with SEQ ID NO: 3; however, those subjects immunized with SEQ ID NO: 1 alone did not show reactivity with SEQ ID NO: 3.

The reactivity to SEQ ID NO: 3 was not seen before vaccination in individuals with a spontaneous immune response to NY-ESO-1. Titration assays showed that T cells specific for SEQ ID NO: 3 recognized the peptide down to concentrations as low as 1 nM. SEQ ID NO: 2 was cross reactive with SEQ ID NO: 3, and was recognized at lower affinities.

The results of these studies are summarized in the tables which follow, using exemplary patients vaccinated or not vaccinated with SEQ ID NO: 1 or 2. In the tables, "S9C" is SEQ ID NO: 1, "S11L" is SEQ ID NO: 2, and "L9L" is SEQ ID NO: 3.

Adeno/ESO represents the adenoviral construct expressing the complete NY-ESO-1 antigen. T cells were stimulated in vitro with autologous pBMCs, either pulsed with the indicated peptide, or which had been transduced with Adeno/ESO.

TABLE 1

| | In vitro stimulation of T cells with: | | | |
|---|---|---|---|---|
| | S9C | S11L | L9L | Adeno/ESO |
| a) Patient NW1288: Pre-existing immunity to NY-ESO-1-Not vaccinated | | | | |
| S9C-tetramer | 1.48% | 1.58% | 0.04% | 1.01% |
| S11L-tetramer | 0.10% | 0.10% | 0.02% | 0.02% |
| L9L-tetramet | 0.03% | 0.17% | 0.04% | 0.03% |
| b) Patient NW866: No pre-existing immunity to NY-ESO-1-Vaccinated with S9C and S11L | | | | |
| S9C-tetramer | 0.04% | 0.06% | ND | 0.13% |
| S11L-tetramer | 0.02% | 0.03% | ND | 0.06% |
| L9L-tetramer | 0.05% | 3.98% | ND | 0.06% |
| c) Patient NW924: Pre-existing immunity to NY-ESO-1-Vaccinated with S9C and S11L | | | | |
| S9C-tetramer | 9.75% | 5.88% | ND | 0.43% |
| S11L-tetramer | 0.09% | 0.13% | 0.02% | 0.02% |
| L9L-tetramet | 0.16% | 5.59% | ND | 0.06% |

TABLE 2

| Study week | S9C-Tetramer | L9L-Tetramer | Elispot T2 + S9C | Elispot T2 + L9L |
|---|---|---|---|---|
| Prestudy | 0.01% | 0.02% | 6(2) | 5(8) |
| Week 2 | 0.00% | 0.07% | 3(1) | 7(4) |
| Week 4 | 0.03% | 0.21% | 2(1) | 42(35) |
| Week 6 | 0.01% | 0.44% | 9(11) | 126(9) |
| End of Study | 0.03% | 2.97% | 1(8) | 289(15) |

Patient P1-E01 develops a response to NY-ESO-1 peptide L9L after vaccination with S9C and S11L.

An additional patient, i.e., P1-E01 representative of subjects with no pre-existing spontaneous immunity to NY-ESO-1 who were vaccinated with SEQ ID NOS: 1 and 2, exhibited significant tetramer staining with SEQ ID NO: 2 but not for SEQ ID NO: 1 tetramers. When contained with activation marker CD62L, the results indicated that CD8$^+$ cells that had been stimulated with SEQ ID NO: 2 had 3 different and distinct patterns. SEQ ID NO: 1 specific cells were CD62L$^+$, while CD8$^+$ cells specific for SEQ ID NOS: 2 and 3 had intermediate, and low CD62L profiles, indicating that SEQ ID NO: 2 could stimulate three distinct CD8$^+$ cell populations, with different activation characteristics.

In an additional set of subjects with pre-existing immunity to NY-ESO-1 (i.e., they were positive for NY-ESO-1 specific antibodies and T cells), who received peptide vaccinations, SEQ ID NO: 3 tetramers were detected as a result of vaccination. These responses to SEQ ID NO: 3 appeared during vaccination alongside existing SEQ ID NO: 1 reactive cells. Table 1c, supra, shows this. When the cells were stimulated with naturally processed NY-ESO-1 from recombinant adenovirus, specific reactivity to SEQ ID NO: 3 was not recalled.

A summary of these results is presented in the table which follows. All patients were HLA-A2$^+$, and vaccination was with both SEQ ID NOS: 1 and 2.

TABLE 3

| RECAP | | | |
|---|---|---|---|
| Peptide used for in vitro stimulation of T cells | | | |
| | S9C | S11L | L9L |
| Patients with natural immunity to NY-ESO-1 | | | |
| S9C | + | + | − |
| S11L | + | + | − |
| L9l | − | − | − |
| Vaccination patients responding only to peptide S11L (no preexisting immunity) | | | |
| S9C | − | − | − |
| S11L | − | + | + |
| L9l | − | + | + |
| Vaccinated patients responding to both peptides S9C and S11L | | | |
| S9c | + | + | − |
| S11l | + | + | + |
| L9L | − | + | + |

T responses to NY-ESO-1 peptides. Patients were HLA-A2$^+$ and vaccination was with peptides S9C and S11L.

EXAMPLE 4

CD8$^+$ T cells taken from patients with spontaneous immunity to NY-ESO-1 were tested for their ability to recognize tumor cells which expressed NY-ESO-1, as well as lymphoblastoid B-cells which had been transfected with the recombinant vaccinia virus expressing NY-ESO-1 described supra. This recognition was in this case for CD8$^+$ cells taken from patients immunized with SEQ ID NO: 1.

When reactivity with SEQ ID NO: 1 was not seen, however, neither was the reactivity pattern with the tumor and NY-ESO-1 expressing EBV-B cells. CD8$^+$ T cells from a patient which were specific for SEQ ID NO: 3 did not recognize the NY-ESO-1 transfected EBV-B cells, and did not produce IFN-γ in response to NY-ESO-1$^+$ cancer cells notwithstanding high levels of expression of the antigen and HLA-A2. This suggests that these cells do not naturally process SEQ ID NO: 3 from full length.

Following treatment of the cancer cells with IFN-γ, which is known to upregulate the cell antigen processing immuno proteosomal digestion, and the antigen presentation (HLA expression) machinery, however, a low level of response to SEQ ID NO: 3 was observed.

This suggested experiments to determine if the IFN-γ treatment was acting at the proteasome level, changing the pattern of processing of the NY-ESO-1. To test this, dendritic cells were used as a source of professional APCs which naturally express the immunoproteasome. To test this, full length NY-ESO-1 protein was administered to dendritic cells in a complex with a monoclonal antibody specific to NY-ESO-1.

Under these conditions, the NY-ESO-1 protein was processed with high efficiency, and T cells specific to SEQ ID NO: 3 showed strong recognition of dendritic cells that had received the immunecomplexes.

The results indicate that SEQ ID NO: 3 requires immunoproteasome action in order to be processed from NY-ESO-1; however, it cannot be produced by constitutive proteasomes of non-professional antigen presenting cells, such as B cells, following transfection with a NY-ESO-1 coding vector.

EXAMPLE 5

The peptides preferably consist of amino acid sequences found in the NY-ESO-1 antigen; however, the invention also includes peptides with similar immunogenic and length characteristics from other molecules, such as tumor antigen, especially cancer testis and differentiation antigen.

This example, and the examples which follow, describe experiments designed to develop a vaccination strategy for treating patients with cancer, using molecules that are processed to tumor rejection antigens, NY-ESO-1 in particular.

Two, 30-mer peptides consisting of amino acid sequencing found in NY-ESO-1 were synthesized, i.e.:

(SEQ ID NO: 4)
ARGPESRLLEFYLAMPFATPMEAELARRSL
and (SEQ ID NO: 5)
LQLSISSCLQQLSLLMWITQCFLPVFLAQP As were additional peptides (SEQ ID NO: 6)
GARGPESRLLEFYLAMPFATPMEAELARRS
and (SEQ ID NO: 7)
HRQLQLSISSCLQQLSLLMWITQCFLPVFLAQ These consist of amino acids 80-109 (SEQ ID NO: 4), 145-172 (SEQ ID NO: 5), 79-109 (SEQ ID NO: 6), and 142-173 (SEQ ID NO: 7), of NY-ESO-1. Within these sequences, amino acids 1-9 of SEQ ID NO: 4 are known to constitute a peptide presented by HLA-Cw6 molecules, and amino acids 13-21 a peptide presented by HLA-Cw3 molecules. See Gnjactic, et al., *Proc. Natl. Acad. Sci. USA*, 97:10917 (2000), incorporated by reference. As for SEQ ID NO: 5, amino acids 13-21, and amino acids 15-23 both constitute peptides presented by HLA-A2. Each of these peptides, when complexed to its partner MHC molecule, is recognized by T cells specific for the resulting complex.

In a first set of experiments, cell line T2 (CEMx721.174.T2) was used. This is an HLA-A*0201 mutant cell line, which lacks TAP transporters. The T2 cells were cultured in RPMI medium 1640, supplemented with 10% fetal calf serum, 2 mM L glutamine, penicillin (100 U/ml), streptomycin (100 µg/ml), and 1% nonessential amino acids. The cells were washed, twice, in X-VIVO-15 medium, to remove serum. Serum free conditions were used throughout these experiments, to minimize the possibility of direct hydrolysis or degradation of polypeptides by serum proteases, as reported by Eberl, et al., *Mol. Immunol.*, 36:103-112 (1999).

The T2 cells were pulsed with varying concentrations (0-100 µm), of one of either the HLA-A2 binding peptides consisting of amino acids 13-21 of SEQ ID NO: 5, or SEQ ID NO: 5, in toto, for anywhere from 1-20 hours, at 37° C. Following incubation, the cells were washed to remove excess peptide and fixed with 1% paraformaldehyde to prevent further processing and membrane cycling. The cells were then used in the ELISPOT assays which follow.

Flat bottomed, 96 well nitrocellulose plates were coated with an IFN-γ specific monoclonal antibody, at 2 µg/ml, and incubated overnight at 4° C. The plates were washed with RPMI, and then blocked with 10% human AB serum for 2 hours, at 37° C.

Presensitized, LAU/157 T cells were added to each well, at a concentration of either $5\times10^4$ or $1\times10^4$ cells/well. LAU/157 T cells are CD8$^+$ T cells which had been developed previously, and are known to be specific for complexes of HLA-A2 and amino acids 13-21 of SEQ ID NO: 5. The LAU/157 cells were presensitized, prior to the ELISPOT assay, in the same manner described in example 1, supra, using the peptide consisting of amino acids 13-21 of SEQ ID NO: 5. A total of $5\times10^4$ target T2 cells, prepared as described supra, were added, and the wells were incubated for 20 hours in RPMI medium 1640, without serum. The plates were then washed thoroughly with water containing 0.5% Tween 20, to remove cells. IFN-γ specific mAbs labeled with biotin (0.2 µg/ml) were added, and incubated for 2 hours at 37° C. The plates were then washed and developed with streptavidin/alkaline phosphotase (1 µg/ml) for 1 hour, at room temperature. Following washing, the substrate 5-bromo-4-chloro-3-indolyl phosphate/nitroblue tetrazolium was added, and incubated for 5 minutes. The plates were washed, and dark violet spots which developed were counted under the microscope.

The results indicated that, despite the absence of TAP transporters, both peptides, the full length polypeptide of SEQ ID NO: 5 and amino acids 13-21 of SEQ ID NO: 5 were presented efficiently to the T cells. Titration assays showed that the full length polypeptide was recognized down to 1 µM, with the nonamer (amino acids 13-21), being recognized down to 10 nM. Since HLA-A* 0201 is the only allele shared by LAU/157 and target T2 cells, the recognition of the full length polypeptide likely occurred through the peptide defined by amino acids 13-21, suggesting that the polypeptide may have been processed by the T2 cells to the smaller peptide defined by amino acids 13-21 of SEQ ID NO: 5.

EXAMPLE 6

In these experiments, HLA-A2 positive, EBV transformed B cells were pulsed with 10 µm of SEQ ID NO: 5 or the peptide consisting of amino acids 13-21 of SEQ ID NO: 5 for 1, 3 or 20 hours, at 37° C. or 4° C. in parallel, the EBV transformed B cells were transfected with vaccinia virus constructs which encoded full length NY-ESO-1, in the same way described supra.

The results indicated that presensitized LAU/157 T cell recognized the full length polypeptide with an efficiency similar to that secured with the peptide defined by amino acids 13-21, or naturally processed NY-ESO-1 expressed by vaccinia; however, the recognition of SEQ ID NO: 5 was time and temperature dependent, with recognition requiring at least 3 hours at 37° C., as compared to the smaller peptide, which was recognized after an hour, at either temperature.

The experiments based on the two different temperatures suggests that internalization of the full length polypeptide was necessary confirming that this polypeptide was likely processed by the cells to the smaller nonamer, while the nonamer could and did bind directly to the cell surface.

EXAMPLE 7

The experiment of example 6 was repeated, using the full length polypeptide of SEQ ID NO: 4, the peptide consisting of amino acids 1-9 of this polypeptide and CD8$^+$ T cell line BE/80, which is known to be specific to complexes of HLA-Cw6 and the nonamer. See Gnjatic, et al., *Proc. Natl. Acad. Sci USA*, 97:10917-10922 (2000), incorporated by reference.

In contrast to SEQ ID NO: 5, SEQ ID NO: 4 was processed and presented after only 1 hour. The presentation was dependent on temperature, which suggested that, while internalization was rapid, it was still required. The different kinetics of processing and presentation may be a reflection of the nonamer peptide's (amino acids 1-9) position within the polypeptide of SEQ ID NO: 4, i.e., N-terminal rather than centrally located.

EXAMPLE 8

These experiments were designed to understand the mechanism by which antigen presenting cells take up polypeptides from exogenous sources, and load them on HLA Class I molecules for presentation.

CD8+ T cell line FW/92 is a known T cell line which is specific for complexes of HLA-Cw*0304 molecules and the peptide consisting of amino acids 13-21 of SEQ ID NO: 4. It was tested with the complete peptide (SEQ ID NO: 4), and the nonapeptide consisting of amino acids 13-21, as described supra, and the experiments were also carried out with pretreatment of the target cells with lactacystin. Lactacystin is known to affect antigen processing by inhibiting proteasomes. See Crain, et al., *J. Biol. Chem.*, 272:13437-13445 (1992).

The results indicated that processing and presentation of amino acids 13-21 of SEQ ID NO: 4 after target cells were pulsed with the complete polypeptide of SEQ ID NO: 4 was rapid, and occurred after 1 hour, but was inhibited by lactasylin treatment. Presentation of the amino acids nonamer peptide, i.e., consisting of amino acids 13-21 by target cells pulsed directly with this nonamer was not impacted by lactasylin. Hence, direct loading of the nonapeptide (amino acids nonamer 13-21 of SEQ ID NO: 4) onto target cells expressing HLA-Cw3 was independent of protealytic action.

In a similar fashion, the processing requirement of SEQ ID NO: 5 were analyzed using another proteasome inhibiting drug, i.e., LnL, which also inhibits proteasomes, and other endoplasmic reticulum peptidases. See Hughes, et al., *J. Exp. Med.*, 183:1569-1578 (1996). LAU/157 T cells again used, and recognition of SEQ ID NO: 5 was abrogated in the presence of the inhibitor, while recognition of cells pulsed directly with the nonapeptide (amino acids 13-21 of SEQ ID NO: 5) remained unaffected.

EXAMPLE 9

The preceding examples demonstrated that there was sensitivity to proteolysis inhibitors, but does not establish a general rule therefor. Lactacystin, e.g., affected the recognition of SEQ ID NO: 4 by FW/92; however, LLnL had an insignificant effect. Both drugs did abolish presentation when the cells were infected with recombinant vaccinia virus that expressed NY-ESO-1. A third drug was tested, i.e., chloroquine, which is known to inhibit endosomal—lysosomal enzymes. See Ziegler, et al., *Proc. Natl. Acad. Sci. USA*, 79:175-178 (1982). It did not appear to effect the presentation of amino acids 13-21 of SEQ ID NO: 4.

These data, including the fact that lactacystin treatment did not affect the presentation of SEQ ID NO: 5, suggests that there are different pathways involved.

EXAMPLE 10

As the preceding experiments demonstrated that polypeptides were taken up by antigen presenting cells and processed into HLA-Class I epitopes, experiments were designed to assess the immunogenicity of NY-ESO-1 polypeptides with peripheral blood lymphocytes from cancer patients who are positive for CD8+ cell activities.

Peripheral blood lymphocytes were obtained from a patient who was HLA-A*0201 positive, with CD8+ T cells specific for complexes of HLA-A2 and the peptide consisting of amino acids 13-21 of SEQ ID NO: 5. The CD8+T cells were pre-sensitized, as described supra, using either the complete polypeptide of SEQ ID NO: 5, or the nonapeptide consisting of amino acids 13-21 of SEQ ID NO: 5. After 10 days of culture, the cells were analyzed using tetrameric complexes of HLA-A2 and the peptide of amino acids 13-21 from SEQ ID NO: 5. These complexes were prepared as described, supra, with the exception of a change in peptide.

The results of the tetramer analysis showed that SEQ ID NO: 5 was able to stimulate T cells against the HLA-A2 epitope as efficiently as the smaller nonapeptide, indicates that both peptides are immunogenic.

Similar results were obtained when PBLs from an HLA-Cw6 positive patient were tested, in the same way, with SEQ ID NO: 4 and the nonapeptide defined by amino acids 1-9 of SEQ ID NO: 4.

EXAMPLE 11

These experiments were designed to determine whether immunogenicity of polypeptides also depended on their processing. This was done in a functional assay that is not dependent on the use of inhibitory drugs.

It was shown, supra, that the peptide defined by amino acids 15-23 of SEQ ID NO: 5 is immunogenic but not naturally processed by tumor cells. In clinical trials, patients developed T cell reactivity to amino acids 15-23 of SEQ ID NO: 5 (SEQ ID NO: 3) as a result of vaccination with a peptide consisting of amino acids 13-23 of SEQ ID NO: 5 (SEQ ID NO: 2), but these T cells fail to recognize B cells transfected with full length NY-ESO-1.

Samples of CD8+ T cells from a patient which were specific to a peptide defined by amino acids 15-23 of SEQ ID NO: 5 and HLA-A2 were tested. They were presensitized with either a peptide defined by amino acids 15-23 of SEQ ID NO: 5, or the peptides of SEQ ID NO: 5 itself, as described supra, and then tested in an ELISPOT assay, also as described supra.

The CD8+ T cells responded strongly to the smaller peptide, but the full length polypeptide did not stimulate CD8+ T cells specific to the smaller peptide, in vitro. Additionally, the CD8+ T cells specific for the smaller peptide (SEQ ID NO: 3) did not recognize the full length molecule, when it was pulsed onto T2 cells, or EBV-B transformed cells.

The results indicate that, just like full length NY-ESO-1, the polypeptide of SEQ ID NO: 5 can be, and is, processed to presented peptides.

The data in examples 1-4, supra, can be seen as setting the stage for the claimed invention, which is set forth for the most part in example 5 et seq.

In examples 1-4, three peptides were tested, i.e., SEQ ID NOS: 1, 2, and 3. As was shown, in in vitro experiments, T cells specific to SEQ ID NOS: 1 and 3 also recognized SEQ ID NO: 2. This is probably because of cross reactivity since, as a longer peptide, SEQ ID NO: 2 encompasses the epitopes of the other molecules. In contrast, SEQ ID NOS: 1 and 3 do not cross react.

Further, it was shown in the experiments set forth in examples 1-4 that SEQ ID NOS: 1 and 2 can and do recall and amplify spontaneous responses following a single, in vitro stimulation. It was shown that patients with natural immunity to NY-ESO-1 are responsive to SEQ ID NO: 1. SEQ ID NO: 2 can recall SEQ ID NO: 1 specific cells in vitro due to the cross reactions described supra. It is also noted that responses specific for SEQ ID NO: 2 never occur in the absence of reactivity for SEQ ID NO: 1. Further, in this more natural setting, SEQ ID NO: 2 does not recall SEQ ID NO: 3 responses.

The responses to SEQ ID NO: 3 occurred as a result of vaccination with SEQ ID NO: 2. No patients with NY-ESO-1 specific spontaneous antibody and T cell immunity antibodies showed spontaneous CD8$^+$ T cell responses to SEQ ID NO: 3. The reactivity is seen, following immunization 7 of patients with no pre-existing NY-ESO-1 immunity with SEQ ID NO: 2. This shows that, in these patients that do not present antibodies to SEQ ID NO: 1 naturally, it is more likely that they will develop T cell reactivity to SEQ ID NO: 3, no following vaccination with the peptide of SEQ ID NO: 2. Reactivity to SEQ ID NO: 3 occurs in patients with natural reactivity to SEQ ID NO: 1, after immunization with SEQ ID NO: 2.

What is intriguing about these data is that, based on predictive algorithms, (see, e.g., Parker, et al., *J. Immunol.*, 152:163 (1994)), SEQ ID NO: 3 should have the strongest binding capacity. Keogh, et al., *J. Immunol.*, 167:787 (2001), and Van der Bruggen, et al., *J. Immunol.*, 156:3308 (1996), have shown that affinity and stability of peptide binding to HLA correlates with their intrinsic immunogenicity, suggesting why SEQ ID NO: 3 is more immunogenic.

Notwithstanding this, predictive software for constitutive proteasome cutting (e.g., Nussbaum, et al., *Immunogenetics*, 53:87 (2001), indicate no cleavage signal after residue 167 of NY-ESO-1, which suggests that SEQ ID NOS: 2 and 3 should not be naturally produced from NY-ESO-1, while residue 165 is in fact a cleavage site, leading to production of SEQ ID NO: 1. This may explain the absence of SEQ ID NO: 3 specific T cells which recognize naturally processed NY-ESO-1, regardless of the manner of presentation.

Yet, SEQ ID NO: 3 specific T cells do recognize NY-ESO-1 when processed and presented by "professional" antigen presenting cells, or by tumor cells induced to express immunoproteasomes after treatment with IFN-γ. SEQ ID NO: 3 appears to be a new epitope, which is a member of a category of peptides that are produced only by immunoproteasomes. See Schultz, et al., *J. Exp. Med.*, 195:391 (2002), incorporated by reference.

Thus, what one sees from the data is the development of SEQ ID NO: 3 as an additional peptide target for NY-ESO-1 specific CD8$^+$ T cells. Vaccination with SEQ ID NO: 3 may be beneficial, because many tumors would express immunoproteasomes rather than constitutive proteasomes, when local IFN-γ levels are high in the tumors. One sees benefit in immunizing with SEQ ID NO: 2 in any event, due to a helper T cell effect in vaccination. SEQ ID NO: 2 is contained completely within a peptide consisting of amino acids 157-170 of NY-ESO-1, and this peptide is recognized by CD4$^+$ T cells, when complexed to HLA-Class II molecule HLA-DP4. See Zeng, et al., *Proc. Natl. Acad. Sci USA*, 98:3964 (2002), incorporated by reference. Both SEQ ID NO: 2 and the peptide defined by amino acids 157-170 of NY-ESO-1 are contained within the polypeptide of SEQ ID NO: 5, at positions 13-23, and 13-25, respectively.

The overall conclusion one derives from examples 1-4 is that in order to select appropriate peptides for immunization predictive approaches which avoid peptides that may not be naturally processed and presented using recombinant vectors, longer synthetic peptides, or even full length proteins must be completed with experimental approaching so that T cell antigenicity and immunogencity may be determined in the context of natural processing and presentation.

Example 5 et seq. relate more directly to the invention, which involves polypeptides which are surprisingly internalized by antigen presenting cells, and then processed to relevant immunogen peptide antigens. Example 5 et seq. show that polypeptides which are clearly too large to bind and to be presented directly by MHC molecules, HLA-A2 molecules in particular, do induce the proliferation of non-americ specific CD8$^+$ T cells. Clearly, this is accomplished by means of internalization by APCs, followed by intracellular processing, such as by intracellular proteases, proteasomes, or some other mode. MHC peptide complex formation and cell surface presentation of such complexes.

It is not at all likely that the positive result demonstrated herein with the polypeptides result from contamination resulting from polypeptide degradation due to extracellular proteases, for instance the examples showed that SEQ ID NO: 3 which is not naturally processed from longer peptides (SEQ ID NO: 5) was not presented, notwithstanding what is clearly high affinity peptide for HLA-A2.

Given that polypeptides require some intracellular processing, the position of class I epitopes within a given polypeptide allows for some flexibility. For example, Gnjatic, et al., *Proc. Natl. Acad. Sci. USA*, 97:10917-10922 (2000), teach that with 18 mer peptides, class I epitopes are recognized from either N- or C-terminal localizations within overlapping polypeptides. Le, et al., *Vaccine*, 19:4669-4675 (2001), showed that when using vaccines based upon multi stranded HLA Class I epitopes from various antigens, individual sequences could be swapped within polypeptide structures, without an affect on immunogenicity.

Thus, the invention involves, inter alia, Isolated polypeptide molecules which consist of from 10 to 40 amino acids, wherein at least one portion of said polypeptide molecule amino acid sequence corresponds to a peptide which binds to an HLA molecule to form a complex that is recognized by a T cell. The invention encompasses MHC-peptide complexes, such as HLA-peptide complexes, recognized by CD4$^+$ and/or CD8$^+$ cells. More preferably, the polypeptides consist of from 15 to 35 amino acids, and most preferably, from 18 to 30 amino acids, such as SEQ ID NO: 4, 5, 6, or 7; however, portions of SEQ ID NO: 4, 5, 6, or 7 which are at least 10 amino acids in length and correspond to the binding epitopes described herein are preferred. A vaccine containing such peptides provides the benefits of multiple immunogenic peptides but avoids complex manufacturing and production problems of full length protein vaccines.

The MHC/HLA binding peptides which are required in the longer peptide molecules may be peptides which bind to one or more of the HLA-A, B or C molecules known to the art and as taught by, e.g., Marsh, et al., The HLA Factsbook (Academic Press 2000), incorporated by reference. The polypeptides may of course naturally contain a plurality of such binding molecules as described by SEQ ID NO: 4, 5; 6, or 7; however, such peptides can be positioned linearly relative to each other (e.g., a polypeptide of 30 amino acids may present an HLA-A2 binding peptide at position 1-9, an HLA-B44 binding peptide at positions 10-19, and an HLA-Cw6 binding peptide at positions 21-29, or may present overlapping epitopes. For example, within the same, 30 mer polypeptide, an HLA-A2 binder may be found at positions 1-9 and an HLA-B44 binder at positions 3-11), and these concepts may be combined in one molecule, with both overlapping and linear binding peptides being available.

The MHC/HLA binding peptides required in the longer peptide molecule may also be peptides that bind to one or more HLA Class I molecules, as shown by, e.g., Marsh, et al., supra, including HLA-DP4. SEQ ID NO: 5 contains both HLA-A (Class I) and HLA-DP4 (Class II) peptides.

The polypeptides can be used, e.g., in connection with antigen presenting cells, such as dendritic cells, which process the polypeptides into peptides which are then combined with HLA molecules. The antigen presenting cells, or "APCs" are chosen such that they present, either inherently or as a result of a recombinant event, HLA molecules with which the relevant peptide structures complex. This can be carried out in vitro, using standard ex vivo dendritic cell techniques known in the art or in vivo, by direct injection of the peptides of the invention using intramuscular, subcutaneous, or intradermal delivery niodes, e.g., either alone or more preferably with adjuvants or immunostimulatory agents known to the art, with patients who present a desired HLA profile on their surfaces.

Also a part of the invention are isolated nucleic acid molecules which encode the relevant polypeptides, as well as expression vectors which include molecules, and recombinant cells which include these constructs, i.e., either the nucleic acid molecules per se, or recombinant vectors including them. In the case of the recombinant cells, these can also be transformed or transfected with one or more HLA molecules, in a manner known to the skilled artisan.

Other aspects of the invention will be known to the skilled artisan and need not be reiterated here.

We claim:

1. An isolated peptide consisting of SEQ ID NO: 4, 5, 6, or 7.

2. An isolated complex of an MHC molecule and the peptide of claim 1.

3. A composition comprising at least two of the peptides of claim 1.

4. An isolated peptide consisting of amino acids 15-23 of SEQ ID NO: 5, or amino acids 1-9 of SEQ ID NO: 4.

5. A composition comprising the peptides of claim 4.

* * * * *

UNITED STATES PATENT AND TRADEMARK OFFICE
CERTIFICATE OF CORRECTION

PATENT NO. : 7,259,235 B2
APPLICATION NO. : 10/493405
DATED : August 21, 2007
INVENTOR(S) : Sacha Gnjatic et al.

It is certified that error appears in the above-identified patent and that said Letters Patent is hereby corrected as shown below:

On The Title Page, Item (22) PCT Filed:, please change "September 26, 2002" to -- September 26, 2003 --

Signed and Sealed this

Eleventh Day of December, 2007

JON W. DUDAS
*Director of the United States Patent and Trademark Office*